United States Patent [19]

Nobuta et al.

[11] Patent Number: 5,608,772
[45] Date of Patent: Mar. 4, 1997

[54] COMPUTERIZED TOMOGRAPHY APPARATUS

[75] Inventors: Yasuo Nobuta, Tochigi-ken; Yusuke Toki, Utsunomiya; Manabu Hiraoka, Tochigi-ken; Naoki Sugihara; Masahiro Ozaki, both of Otawara, all of Japan

[73] Assignee: Kabushiki Kaisha Toshiba, Kawasaki, Japan

[21] Appl. No.: 539,707

[22] Filed: Oct. 5, 1995

Related U.S. Application Data

[62] Division of Ser. No. 347,236, Nov. 23, 1994.

[30] Foreign Application Priority Data

| Nov. 26, 1993 | [JP] | Japan | 5-296346 |
| Apr. 5, 1994 | [JP] | Japan | 6-067343 |
| Oct. 31, 1994 | [JP] | Japan | 6-267280 |

[51] Int. Cl.[6] .................................. G06T 11/00
[52] U.S. Cl. ........................ 378/16; 378/15; 378/116
[58] Field of Search ............... 375/15, 16, 20, 375/114, 115, 116, 4

[56] References Cited

U.S. PATENT DOCUMENTS

| 4,773,086 | 9/1988 | Fujita et al. | 378/116 X |
| 4,789,929 | 12/1988 | Nishimura et al. | |
| 5,046,003 | 9/1991 | Crawford | 378/15 X |
| 5,212,737 | 5/1993 | Ackelsberg | |
| 5,321,651 | 7/1993 | Ozaki et al. | |
| 5,386,446 | 1/1995 | Fujimoto et al. | 378/15 X |

FOREIGN PATENT DOCUMENTS 2499734   8/1982   France.

*Primary Examiner*—David P. Porta
*Attorney, Agent, or Firm*—Oblon, Spivak, McClelland, Maier & Neustadt, P.C.

[57] ABSTRACT

A computerized tomography apparatus is disclosed which reconstructs a tomography image of data from multi-directional projection data in a period of time less than the time required for a scan operation for data acquisition and displays the tomography image after a lapse of a given period of time from the termination of the scan operation. This avoids the time interval between scan and image display becoming irregular. Accordingly, tomography images can be displayed successively like motion picture to observe the internal movements of a section of a human body under examination in real time.

5 Claims, 12 Drawing Sheets

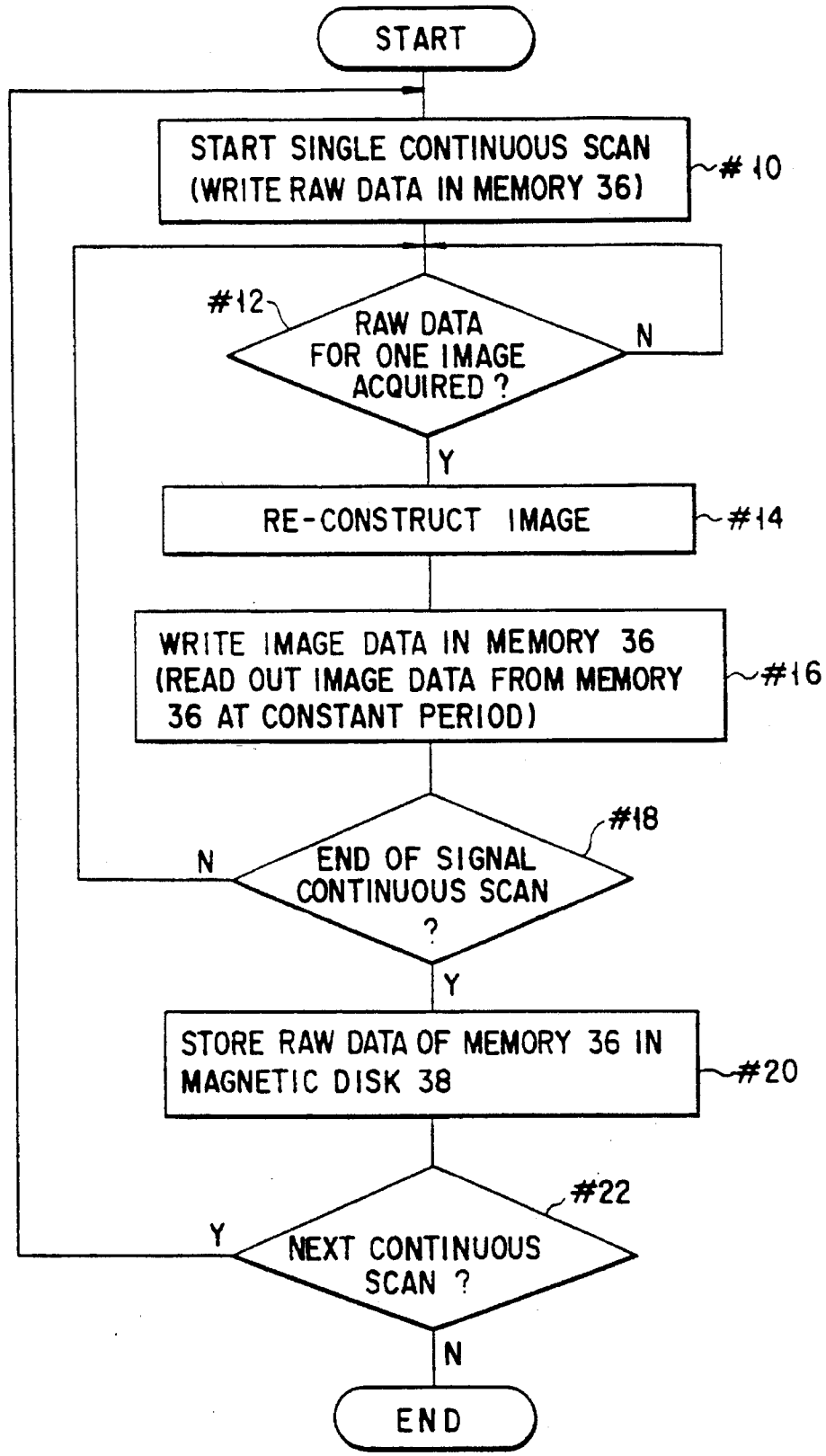
F I G. 1

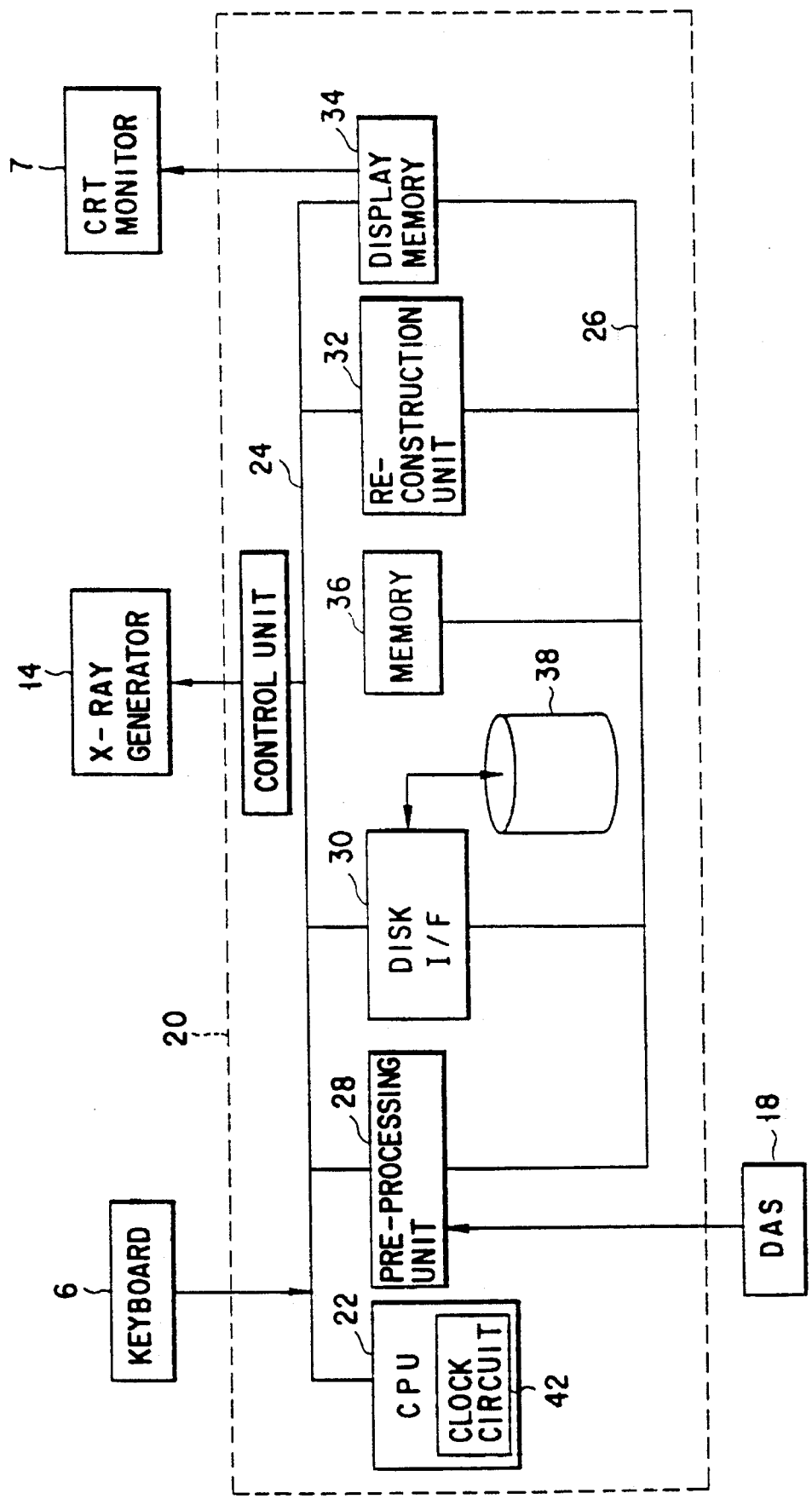
F I G. 4

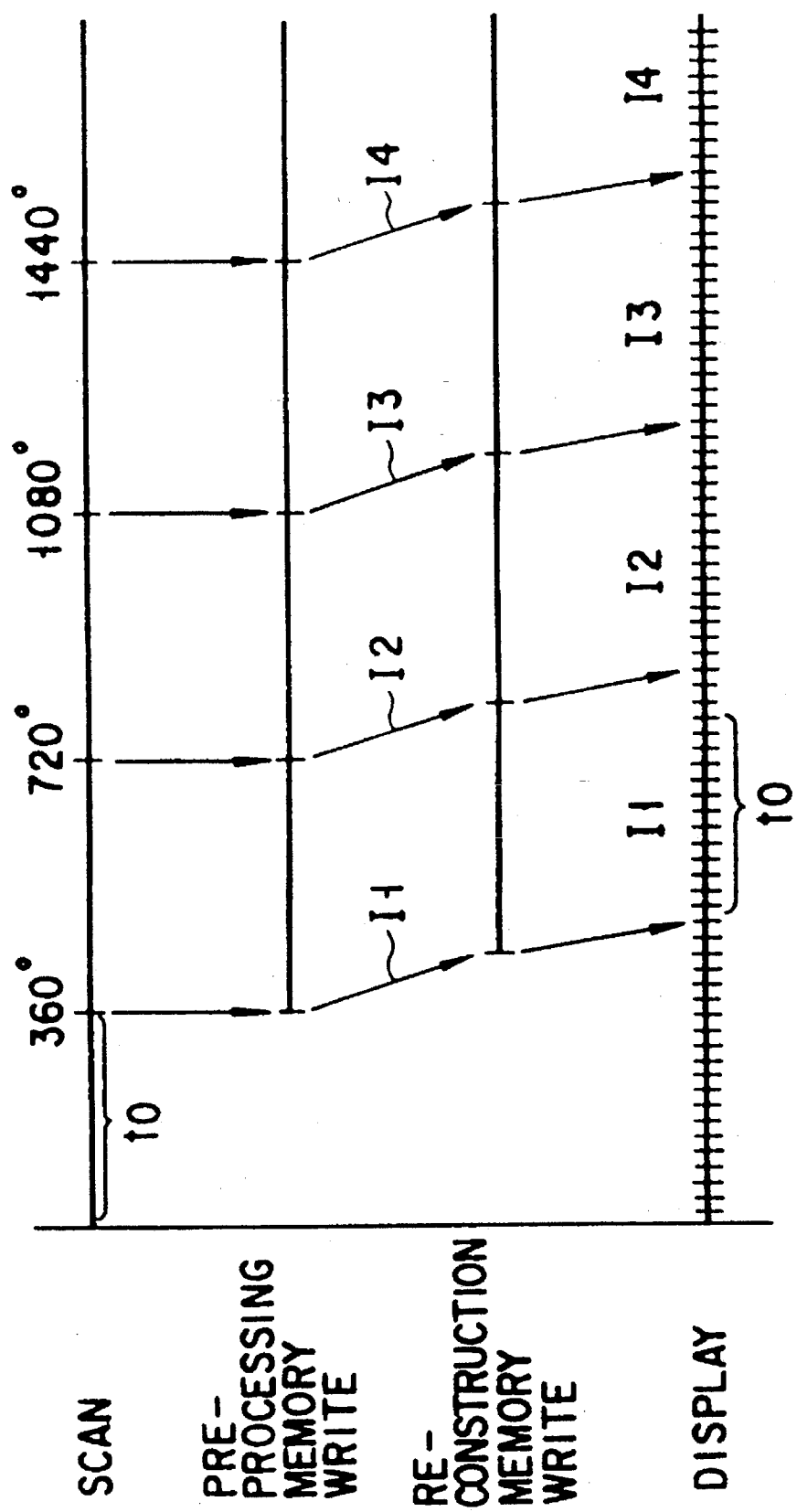
F I G. 5

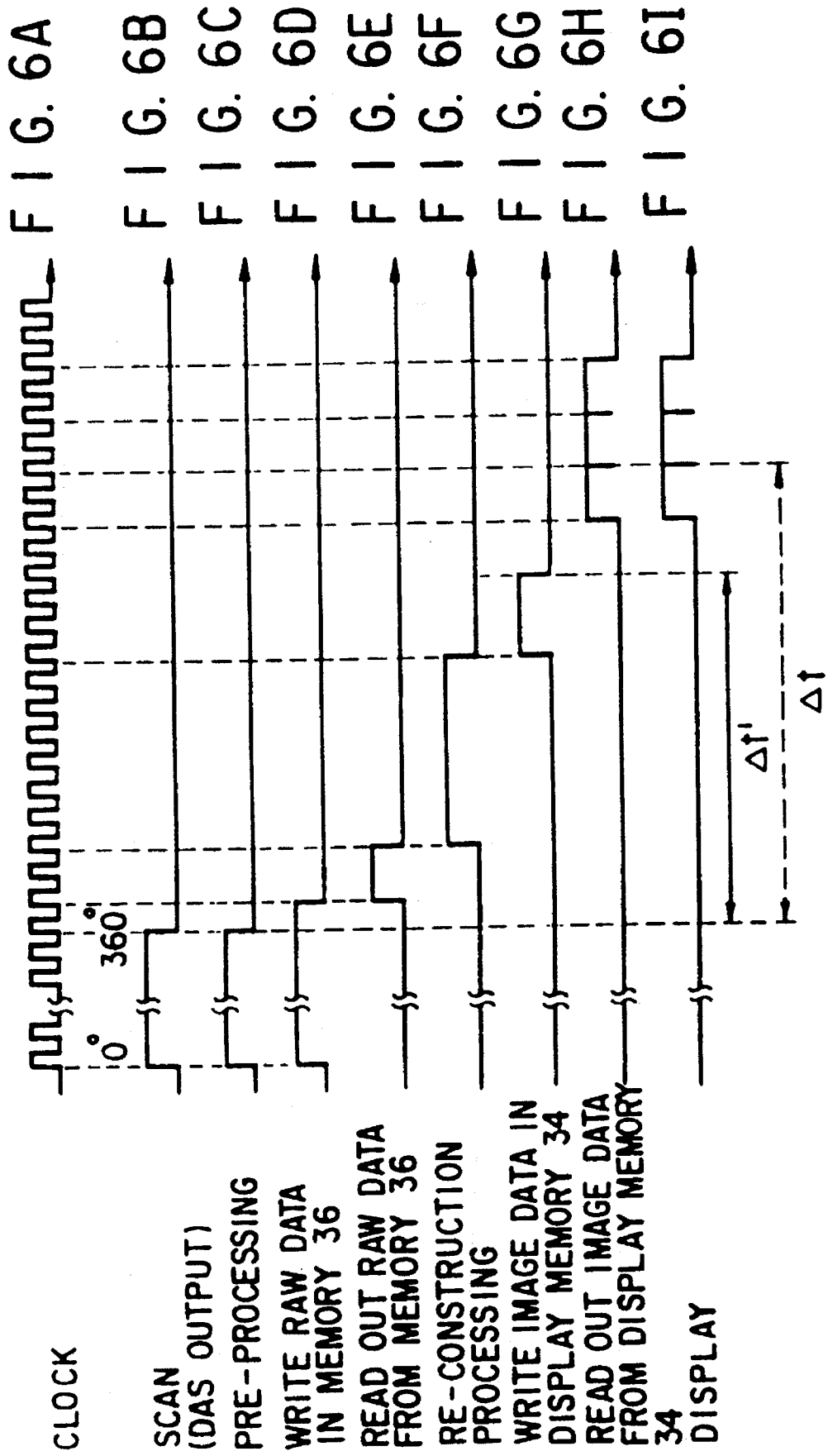

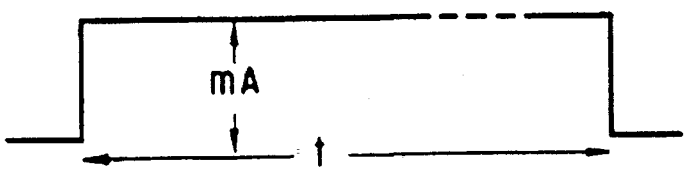
FIG. 9A CONTINUOUS X-RAYS
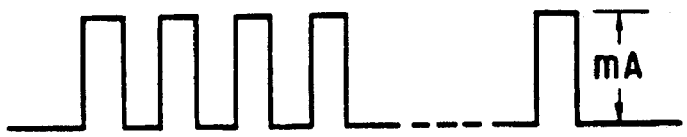
FIG. 9B PULSED X-RAYS
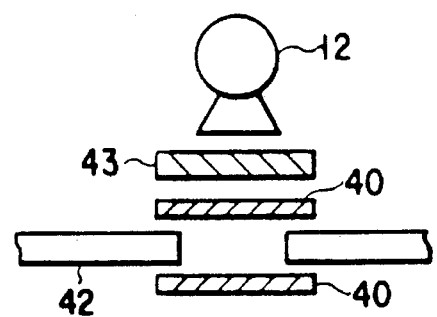
FIG. 10
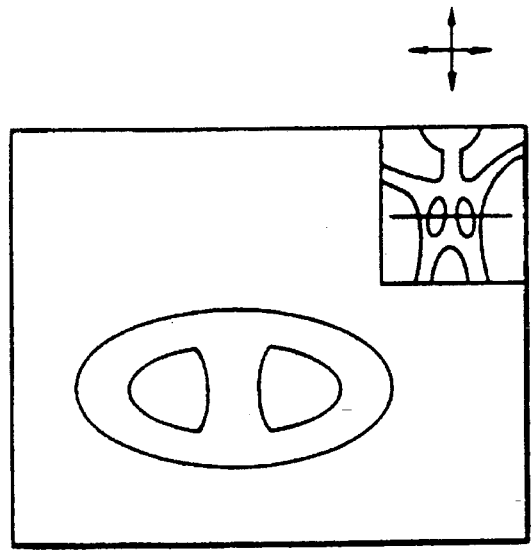
FIG. 12

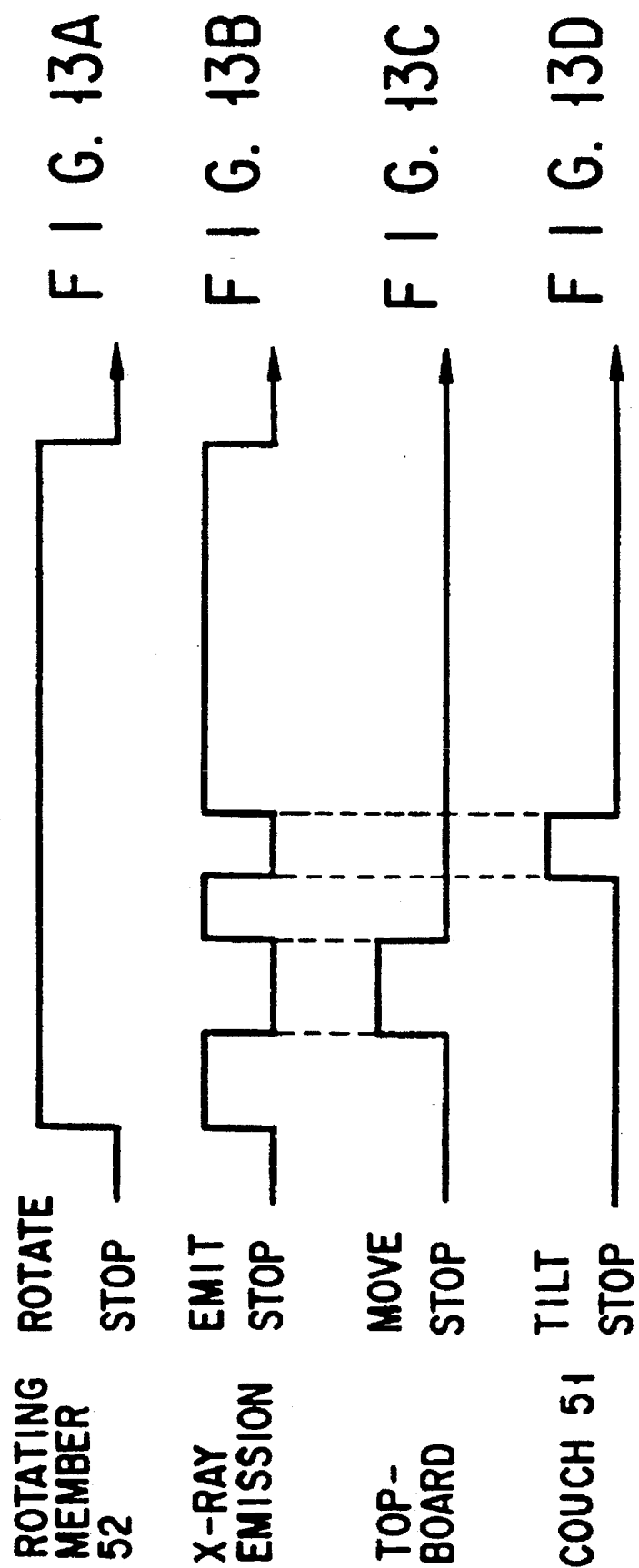

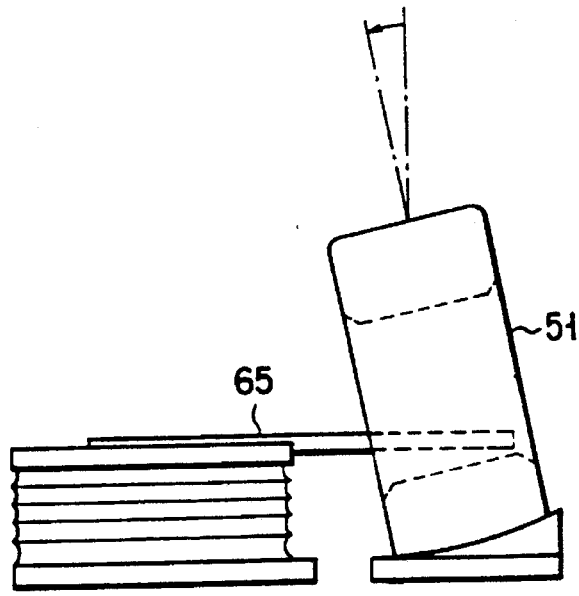
F I G. 14
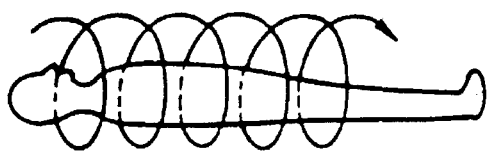
F I G. 16A
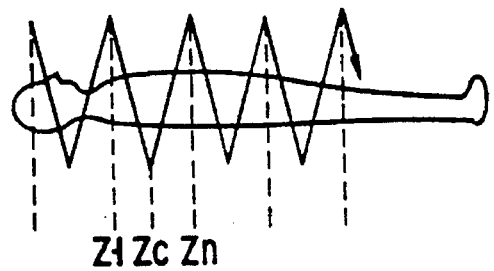
F I G. 16B

COMPUTERIZED TOMOGRAPHY APPARATUS

This is a Division, of application Ser. No. 08/347,236 filed on Nov. 23, 1994.

BACKGROUND OF THE INVENTION

1. Field of the Invention

The present invention relates to a computerized tomography apparatus. More specifically, the present invention relates to a computerized tomography apparatus which permits continuous scanning.

2. Description of the Related Art

In general, a computerized tomography (CT) apparatus performs three processes of scanning, image reconstruction and image display in time sequence. Projection data, acquired from many directions while an X-ray tube rotates or the X-ray tube and a detector array rotate together, is digitized, then subjected to preprocessing, such as calibration, and temporarily stored as raw data on large-volume storage, such as magnetic disk storage.

At the time of image reconstruction, the raw data is read out of the magnetic disk storage, then fed into a reconstruction unit via a memory. Tomography image data reconstructed in the reconstruction unit is stored on magnetic disk storage and transferred as a video signal to a cathode ray tube (CRT) monitor via a display memory.

The introduction of slip rings has enabled a continuous scan to be made. This continuous scan permits multi-directional projection data for a single slice or multiple slices to be obtained in time sequence. The multi-direction projection data is read from the magnetic disk storage into the reconstruction unit at arbitrary timing, then used for image reconstruction as described above. The time required for the image reconstruction is longer than the scanning time, and the time it takes to write to and access to the magnetic disk storage also is long. It is therefore impossible to display tomography images successively in real time like motion pictures while making a continuous scan.

The high-speed processing of image reconstruction was considered in recent years and is reaching the stage of practical use. Thus, the CT apparatus has been expected to display successively tomography images in real time while making a continuous scan. However, the long storage and access times of magnetic disk storage are serious obstacles to practical use of the high-speed processing of image reconstruction. Further, the wait state occurs irregularly in writing to and accessing magnetic disk storage. Thus, the time interval between a scan and the display of a tomography image varies irregularly, making it impossible to reproduce the internal movements of a section of a human body under examination.

Besides, the following problems arise in connection with the use of real-time X-ray CT apparatus in a clinical field. The first problem is that it takes a long time for an operator to place a slice or cross section of interest of a subject under examination in position by manually moving a top board on which the subject lies while watching a cross beam of light projected onto the subject from a projector. The second problem is that, when a scan that involves the movement of a top board (e.g., a helical scan, a multi-slice scan or the like) is suspended, it takes a long time to restart it. This is because a piece of work is required at the time of restart to put back the top board manually so that a slice of interest will be placed in the position at the time of suspension of the scan.

SUMMARY OF THE INVENTION

It is therefore an object of the present invention to provide a computerized tomography apparatus which permits the internal movements of a section of a subject under examination to be displayed in real time during a scan.

It is another object of the present invention to provide a computerized tomography apparatus which allows an operator to correct the position of a planar slice of interest of a human body by a simple operation while observing tomography images in real time.

It is still another object of the present invention to provide a computerized tomography apparatus which, at the time of restart of computerized tomography after suspension of it, automatically puts back a top board on which a subject under examination lies so that a slice of interest of the subject will be placed in the position at the time of suspension of the tomography.

According to a first aspect of the present invention there is provided a computerized tomography apparatus comprising: data acquisition means for acquiring multi-directional projection data on a subject under examination by means of a scan operation; image reconstructing means for reconstruction tomography image data from the multi-directional projection data in a period of time less than a time required for the scan operation; and display means for displaying the tomography image data after a lapse of a given period of time from the termination of the scan operation.

According to a second aspect of the present invention there is provided a computerized tomography apparatus comprising: data acquisition means for acquiring first and second multi-directional projection data successively by performing a first and a second scan operation successively; image reconstruction means for reconstructing first tomography image data from the first multi-directional projection data in a period of time less than a time required for the first scan operation and reconstructing second tomography image data from the second multi-directional projection data in a period of time less than a time required for the second scan operation; and display means for displaying the first tomography image data and displaying the second tomography image data after a lapse of a given period of time from the time the first tomography image data is displayed.

According to a third aspect of the present invention there is provided a computerized tomography apparatus which permits a scan operation for acquiring multi-directional projection data required to reconstruct a single tomography image of data to be performed continuously, comprising: means for selectively switching a mode of operation performed by the computerized tomography apparatus between a continuous scan mode in which the scan operation is performed continuously to reconstruct tomography images of data successively and reconstructed tomography images are displayed successively after a lapse of a predetermined period of time from the termination of a first scan operation and a single scan mode in which the scan operation is performed once to reconstruct a single tomography image of data and the single tomography image is displayed.

According to a fourth aspect of the present invention there is provided a computerized tomography apparatus comprising: acquisition means for acquiring projection data required to reconstruct a tomography image of data successively; reconstruction means for reconstructing tomography images of data successively from projection data acquired by the acquisition means; display means for displaying tomography images reconstructed by the reconstruction means successively; a couch for supporting a top board on which a subject under examination is laid down so that it can move in one direction means for taking a scanogram that is an X-ray projection image of the subject under examination viewed from a direction; means for displaying the scanogram with a line cursor; input means for changing the position of the line cursor on the scanogram and control means for controlling the couch so that the top board is moved to a position where a slice of interest of the subject under examination corresponds in position to the line cursor on the scanogram.

According to a fifth aspect of the present invention there is provided a computerized tomography apparatus comprising: acquisition means for acquiring projection data required to reconstruct a tomography image of data successively; reconstruction means for reconstructing tomography images of data successively from projection data acquired by the acquisition means; display means for displaying tomography images reconstructed by the reconstruction means successively after a lapse of a given period of time from the acquisition of the projection data a couch for supporting a top board on which a subject under examination is laid down so that it can move in one direction; control means for causing the acquisition means to acquire the projection data while moving the top board; and input means for inputting an Interrupt instruction to interrupt the acquisition of the projection data, the control means being responsive the Interrupt instruction from the input means to instruct the acquisition means to interrupt the acquisition of the projection data and to put back the top board so that a slice of the subject under examination for which the latest tomography image data was acquired is placed in the position at the time of the acquisition of the last tomography image data.

The computerized tomography apparatus according to the first aspect of the present invention reconstructs a tomography image of data from multi-directional projection data in a period of time less than the time required for a scan operation for data acquisition and displays the tomography image after a lapse of a given period of time from the termination of the scan operation. This avoids the time interval between scan and image display becoming irregular. Therefore, tomography images can be displayed successively like motion picture to observe the internal movements of a section of a human body under examination in real time.

The computerized tomography apparatus according to the second aspect of the present invention reconstructs a tomography image of data in a period of time less than the time required for a scan operation for data acquisition and makes the time difference between a first tomography image of data being displayed and a second tomography image of data being displayed equal to the time difference between first multi-directional projection data being acquired and second multi-directional projection data being acquired. Therefore, tomography images can be displayed successively like motion picture to observe the internal movements of a section of a human body under examination.

The computerized tomography apparatus according to the third aspect of the present invention permits either a continuous scan mode or a single scan mode to be carried out selectively as needed. In the continuous scan mode, a scan operation is performed continuously, tomography images of data are reconstructed successively, and the tomography images are displayed successively after a lapse of a given period of time from the termination of the first scan operation. Therefore, the tomography images can be displayed successively in real time like motion picture.

The computerized tomography apparatus according to the fourth aspect of the present invention permits a line cursor to move on a scanogram of a human body under examination. The line cursor on the scanogram corresponds in position to a planar slice of a human body to be examined by tomography. The position of the line cursor on the scanogram can be changed easily by an operator, whereby a change from a slice to another is made. Thus, by moving the top board, a planar slice of interest of a human body to be examined is placed in position for tomography.

According to the computerized tomography apparatus of the fifth aspect of the present invention, when the acquisition of projection data is interrupted, the top board is permitted to return automatically so that the 10 slice for which the latest tomography image of data was acquired is placed in the tomography position. Thus, the acquisition of projection data can be restarted immediately.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a flowchart for the single scan mode in a first embodiment of the present invention

FIG. 4 is a block diagram of a CT control unit;

FIG. 5 illustrates the procedure in the continuous scan mode

FIG. 6 illustrates the procedure from data acquisition to display for a single tomography image;

FIG. 9 illustrates pulsed x-rays used to reduce the amount of irradiation of a human body under examination with X-rays;

FIG. 10 illustrates a filter adapted to reduce the amount of irradiation of a human body under examination with X-rays

FIG. 12 illustrates an example of a display screen;

FIG. 13 illustrates timing by which operations of rotating the rotation unit, emitting X-rays, moving the top board, and tilting the gantry are performed;

FIG. 14 illustrates a tilt of the gantry;

FIG. 15 is a block diagram of a computerized tomography apparatus according to a third embodiment of the present invention and FIGS. 16A and 16B illustrate an orbit of the X-ray tube around a human body under examination in a herical scan.

DETAILED DESCRIPTION OF THE PREFERRED EMBODIMENTS

Figure 2:
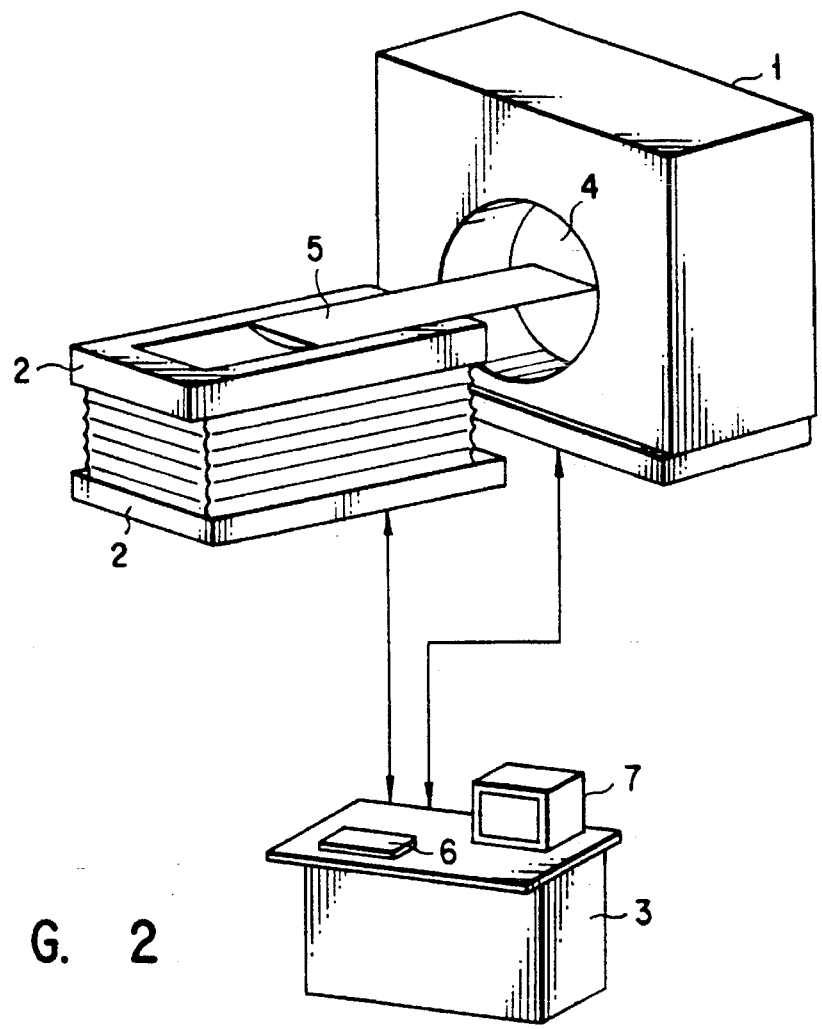
FIG. 2 is an exterior view of an X-ray computerized tomography apparatus.

Referring now to FIG. 2, there is illustrated schematically a computerized tomography apparatus according to a first embodiment of the present invention. This computerized tomography apparatus is composed of a gantry 1, a couch 2, and an operating console 3. The gantry 1 has a central aperture 4 to which a human body under examination is allowed to have access. The couch 2 is placed in front of the gantry 1, which is electrically driven so that its height can be adjusted. On the top of the couch 2 is placed a slidable top board 5 on which the subject under examination is to be laid down. The top board 5 is electrically driven to travel on the top of the couch toward the gantry 1. Though not shown, the gantry 1 is provided underneath with castors so that it can be moved manually toward the couch 2. The reason is that tomography may be used simultaneously with an operation and, in that case, it is desirable from the viewpoint of safety to place a slice of interest of the human body in position for examination by moving the gantry 1 rather than by moving the top board 5. Of course, the top board can be moved to place the slice in position. Note that, in the continuous scan mode, the slice position is generally changed only by moving the top board 5.

On the top of the console 3 are placed a keyboard (a mouse may be included) 6 and a CRT monitor 7. A control unit is housed in the console 3. This control unit is connected to both the gantry 1 and the couch 2.

Figure 3:
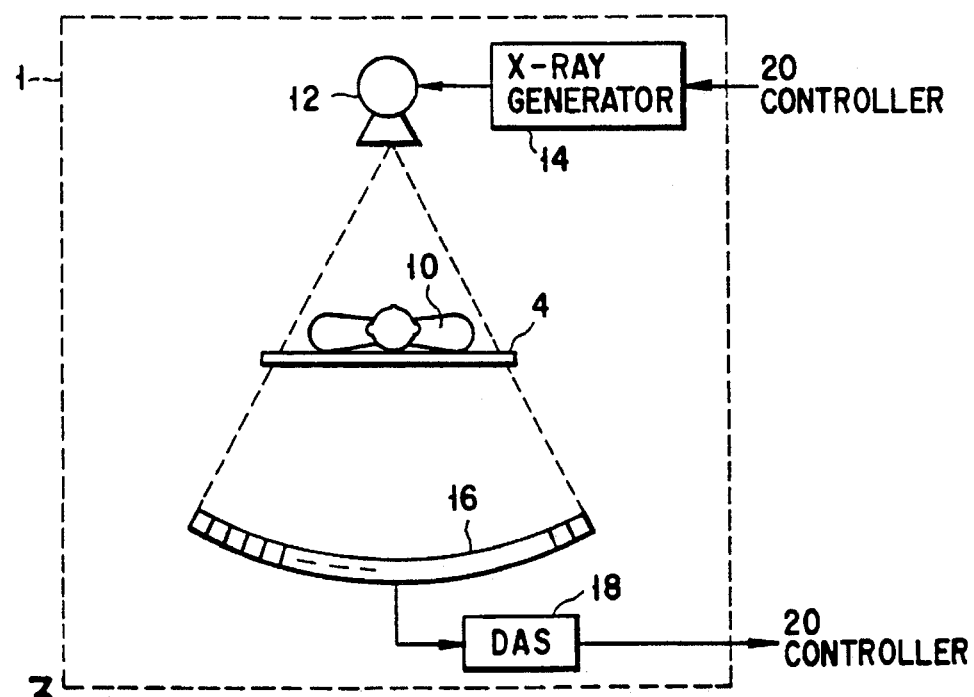
FIG. 3 is a schematic illustration of the structure of the gantry shown in FIG. 1.

As shown in FIG. 3, the gantry 1 includes therein an X-ray tube 12 which emits an X-ray beam in the form of a fan to a subject under examination 10 laid down on the top board 5 and a multi-channel X-ray detector array 16 which has a great number of detector elements arrayed in the form of a circular arc with center at the focus of the X-ray tube and detects X-rays transmitted through the subject 10. The X-ray tube and the X-ray detector array are supported by a rotating member so that they can make continuous rotation around the subject 10 while facing each other with the subject interposed therebetween. The X-ray tube and the detector array are electrically connected to a fixed member via slip rings. Thereby, multi-directional projection data on the subject 10 required to reconstruct a single tomography image can be acquired continuously as long as the x-ray tube 12 and the detector array 16 makes continuous rotation around the subject. When the X-ray tube and the detector array rotate around the same slice of a human body, a so-called dynamic scan is made by which changes in a tomography image due to inflow and outflow of a contrast medium can be traced. When a change from a slice to another is made in synchronism with the rotation of the X-ray tube and the detector array, a so-called herical scan is made. The computerized tomography apparatus of this type is referred to as the third-generation (R/R type) CT apparatus. The CT apparatus is not limited to this type. Use may be made of the fourth-generation (R/S type) CT apparatus in which X-ray detector elements are arranged to surround a subject under examination over a range of 360 degrees and an X-ray tube alone is rotated or the fifth-generation (S/S type) CT apparatus in which, in addition to X-ray detector elements, a number of X-ray tubes are arranged to surround a subject under examination over a range of 360 degrees.

In the gantry 1 is installed an X-ray generating device 14 which is connected to the X-ray tube 12 via slip rings and supplies a tube current and tube voltage to the X-ray tube continuously or in the form of a pulse, thereby causing the X-ray tube to emit X-rays. Also, a data acquisition system (DAS) 18 is installed in the gantry 1 and connected to the detector array 16. This data acquisition system 18 is composed of integrators for integrating output signals of the respective detector elements in the detector array 16, a multiplexer for taking in output signals of the respective integrators at a high speed, in serial form, on a channel-by-channel basis, and an analog-to-digital converter for converting an output signal of the multiplexer to a digital signal, thereby outputting projection data in which X-ray transmission of each X-ray path (channel) is reflected.

FIG. 4 is a block diagram of the control unit 20 within the console 3. A central processing unit (CPU) 22 is provided which serves as a host controller. A control bus 24 and a data bus 26 are coupled to the CPU 22. The CPU 22 has a clock circuit 42 built in and controls operations and timing in each of components in the control unit 20 by means of clock pulses from the clock circuit. To the control bus 24 are connected a preprocessing unit 28, a disk interface (disk I/F) 30, a reconstruction unit 32, and a display memory 34. The keyboard 6 and the X-ray tube 14 described above are also connected to the control bus 24. To the data bus 26 are connected the preprocessing unit 28, the disk I/F 30, the reconstruction unit 32, the display memory 34, and a memory 36. To the disk I/F 30 is connected a magnetic disk drive 38 serving as large-volume storage. The data acquisition system 18 is connected to preprocessing unit 28. The projection data from the data acquisition system 18 is subjected to preprocessing such as calibration in the preprocessing unit, then temporarily written into the memory 36 such as a DRAM. The projection data is read from the memory 36 into the reconstruction unit 32, which reconstructs tomography image data from the multi-directional projection data. The resultant image data is temporarily written into the display memory 34 such as a DRAM. The image data is then read from the memory 34 and fed into the CRT monitor 7, whereby a tomography image is displayed. The image data read from the display memory 34 is also written on a magnetic disk in the disk drive 38 via the disk I/F 30.

Next, the operation of the present embodiment will be described. FIG. 1 is a flowchart for the continuous scan mode. FIG. 5 illustrates the flow of operations from scan to display in the continuous scan mode. As described above, the present embodiment has cinetomography and single scan modes as modes of operations, one of which is selected as requested by an operator through the keyboard 6.

when an operation is started, the X-ray tube 12 and the detector array 16 start rotating continuously, whereby a continuous scan is started. The continuous scan is defined by repeating a scan operation continuously. The scan operation is defined as an operation to acquire multi-directional projection data required to reconstruct a single tomography image while the X-ray tube 12 and the detector array 16 are rotating. During the continuous scan, the slice position may be fixed or changed. As will be described later, according to the present embodiment, data acquisition, image reconstruction and image display are performed at high speed as a set of operations, and the time interval (time differential) from the time a scan operation is performed to acquire projection data for a single image to the time when that image is displayed is the same for all scan operations. This prevents the internal movements of the slice of a human body under examination from becoming difficult to observe in real time due to the irregularity of the time interval between the moment that an scan operation is terminated and the moment that a corresponding image is displayed resulting from the presence of some delays involved in writing into and read from the memories 34 and 36. For this reason, tomography images can be displayed almost in real time like motion pictures. For example, this continuous scan mode is performed so as to check the arrival of the tip of a nyxis needle at a tumor during nyxis treatment by watching successive tomography images obtained by a continuous scan. In this case, the slice position remains unchanged throughout the continuous scan. The continuous scan mode may be used to position a selected slice for usual tomography. In this case, it will be needed to be able to change the slice position at will. The slice position may be changed by sliding the top board 5. However, when the continuous scan mode is used during an operation, the slice position should preferably be changed by sliding the gantry 1 because it is not desirable to move a patient to whom various tubes and instruments are attached. In this case, the gantry 1 is preferably equipped with a power assist mechanism which permits a doctor to move it manually. In the continuous scan mode, there is no need to change the slice position at a constant speed as in a usual helical scan. The slice position may alternate irregularly between being fixed and being changed. Further, the slice position may be changed at varying speeds.

During a scanning operation, the projection data acquired by and output from the data acquisition system 18 is subjected to preprocessing, such as calibration, in the preprocessing unit 28, then written into the memory 36 as raw data. For example, the rotational speed of the X-ray tube 12 and the detector array 16 is selected to be one rotation per second and a single continuous scan operation is determined to have a period of 50 seconds, during which time the X-ray tube and the detector array make 50 rotations. This period is determined in order not to exceed the allowable limit that is determined from the standpoint of the heat-resisting property of the X-ray tube and safety against exposure of human bodies to X-rays. Supposing that 2M bytes of raw data are acquired in one rotation, then the memory 36 will have a storage capacity of about 100M bytes in order to store all raw data for a single continuous scan. The display memory 34 has a storage capacity to store multiple tomography images obtained by a single continuous scan.

In step #12, the CPU 22 makes a decision of whether raw data required to reconstruct a single tomography image has been obtained. If the raw data has been obtained, the procedure goes to step #14 in which the raw data is transferred from the memory 36 to the reconstruction unit 32. The scan is made continuously. The use of the memory 36 to transfer the raw data from the data acquisition system 18 to the reconstruction unit 32 makes it possible to reduce considerably the interval that elapses from the time the scan is started to the time when the reconstruction processing is started as compared with the use of a magnetic disk having long access times. Conventionally, all raw data is temporarily stored on a magnetic disk, then read in a spare time and reconstructed. This requires a long time between the moment that a scan operation is started and the moment that the reconstruction processing is started, failing in real-time processing.

Fast processing is used in which the processing time in the reconstruction unit 32 is made shorter than the scanning time (data acquisition time). This prevents a time lag between the time a scan operation is completed and the time the reconstruction of a tomography image is completed, or a time difference between the time the acquisition of projection data required to reconstruct a tomography image is completed and the time the reconstruction of a tomography image using that projection data is completed, from increasing each time a scan is repeated. For the fast processing, the reconstruction unit 32 uses multiple processors in parallel and processes raw data on a view-by-view basis or on a channel-by-channel basis (in general, one detector element corresponds to one channel), thereby performing the reconstruction processing in parallel. The more the processors, the more the processing speed increases. In addition, the higher the clock rate, the more the processing speed increases.

In order to implement fast reconstruction processing, the present embodiment further adopts a way of reducing (by partially removing or by bunching) the number of views per rotation (360 degrees). For example, in the usual single scan mode, projection data of 900 views per rotation is acquired (i.e., the data acquisition system 18 repeats data acquisition in 900 cycles for one rotation), while, in the continuous scan mode, data acquisition is repeated at a rate of 450 views per rotation. In the continuous scan mode, therefore, the spatial resolution of tomography images will be reduced. However, since the purpose of the continuous scan mode is to observe the internal movements of a human body almost in real time, no problem will arise from the reduced spatial resolution of images. High-resolution tomography images can be obtained in the usual photography mode. Further, in order to reduce the reconstruction time, the number of pixels may be decreased in the reconstruction processing. In the usual single scan mode, a single tomography image is reconstructed in a size of 512×512 pixels and displayed in that size. In the continuous scan mode, on the other hand, a tomography image is reconstructed in a size of 256×256 pixels, and the number of pixels for display is increased to 512×512 pixels by interpolation, permitting the processing time to be reduced.

In the continuous scan, tomography images are reconstructed one after another. In this case, assuming that a single tomography image is reconstructed every rotation and the rotational speed of the X-ray tube and the detector array is one rotation per second, then tomography images will be reconstructed at a rate of one per second. In order to increase the reconstruction rate, a technique disclosed in Unexamined Japanese Patent Publication KOKAI No. 4-266744 can be applied to the present embodiment. According to this technique, each time the x-ray tube and the detector array rotate through a small angle of $\alpha°$ (e.g., 10°), a partial image is reconstructed from projection data for 10°. By adding 36 partial images for 360° together, a complete tomography image for 360° is produced. Further, after a tomography image has been produced, addition of the latest partial image to that tomography image and subtraction of the oldest partial image from that tomography image are repeated. Thereby, a new tomography image will be produced each time the X-ray tube and the detector array rotate through 10°, which permits tomography images to be obtained in succession at a high reconstruction rate. Alternatively, a technique disclosed in Unexamined Japanese Patent Publication KOKOKU No. 1-23136 may be adopted in order to increase the reconstruction rate. This technique obtains tomography image information from projection data for an image by back projection. Differential data between the latest projection data obtained immediately after that projection data and a portion of that projection data corresponding in position to the latest projection data is back projected onto the reconstructed image information. This permits the next reconstructed image information delayed in time to be produced at a high speed. Both the techniques involve a concept of updating a tomography image once reconstructed with time. Other techniques which are extensions to those techniques may be used to further increase the reconstruction rate.

Upon completion of reconstruction, tomography image data is written into the display memory 34 in step #16. Until the next tomography image is displayed, the current tomography image data is read from the display memory 34 repeatedly at regular intervals of time and transferred to the CRT monitor 7 so that the current tomography image is displayed frozen on the CRT monitor. Such a display method is the same as cinedisplay (motion picture display; cinefluoroscopy) used in fluoroscopic apparatuses. If the next tomography image data were written into the display memory while it is read of data, information would vary between the top and bottom of an image. It is thus needed to delay writing into the display memory until reading from that memory is completed.

In step #18, a decision is made in the CPU 22 as to whether a single continuous scan is completed, i.e., whether 50 seconds has elapsed since the commencement of the scan operation. If the scan operation is not completed, the procedure returns to step #12 for acquisition of data required to reconstruct the next tomography image; otherwise, the procedure goes to step #20 in which raw data in the memory 36 is written on the magnetic disk in the disk drive 38. If the raw data need not be retained, step #20 can be omitted. In step #22, a decision is made as to whether the next continuous scan is to be made. If the next scan is to be made, the procedure returns to step #10; otherwise, the procedure comes to an end.

After the termination of a continuous scan operation, the memory 36 stores raw data obtained by at least the last scan. To display a tomography image after the termination of the continuous scan operation, the raw data in the memory can be used for image reconstruction. In the continuous scan mode, as described above, tomography images can be observed almost in real time. Thus, they may be used as support images for a doctor during an operation. However, it is often difficult for the doctor to watch the monitor during the operation. In such a situation, an assistant can provide various instructions to the doctor while watching the monitor. The doctor may want to observe the progress of nyxis after the termination of a single continuous scan. After the termination of the continuous scan, the last tomography image is frozen and raw data is read from the memory 36 and reconstructed as instructed by the doctor, whereby images are displayed frame by frame.

Next, the operations from the acquisition of data for a single tomography image to display thereof will be described in detail. FIG. 6 is a timing diagram for this operation. The data acquisition system 18 provides projection data each time the X-ray tube 12 and the detector array 16 rotate through a given small angle. The projection data is written into the memory 36 via the preprocessing unit 28. After all projection data for all angles (0° to 360°) required to reconstruct a single tomography image is written into the memory 36, the projection data is read from the memory 36, then transferred to the reconstruction unit 32. In the reconstruction unit, the tomography image data is reconstructed at a high speed, i.e., in a period of time shorter than the data acquisition time, then written into the display memory 34. During this period of time, no access is made to the disk drive 34. The tomography image data is read from the display memory 34, then sent to the CRT display unit 7. As described above, the reading of the tomography image data from the display memory 34 is repeated until the next tomography image is displayed.

Figure 7A:
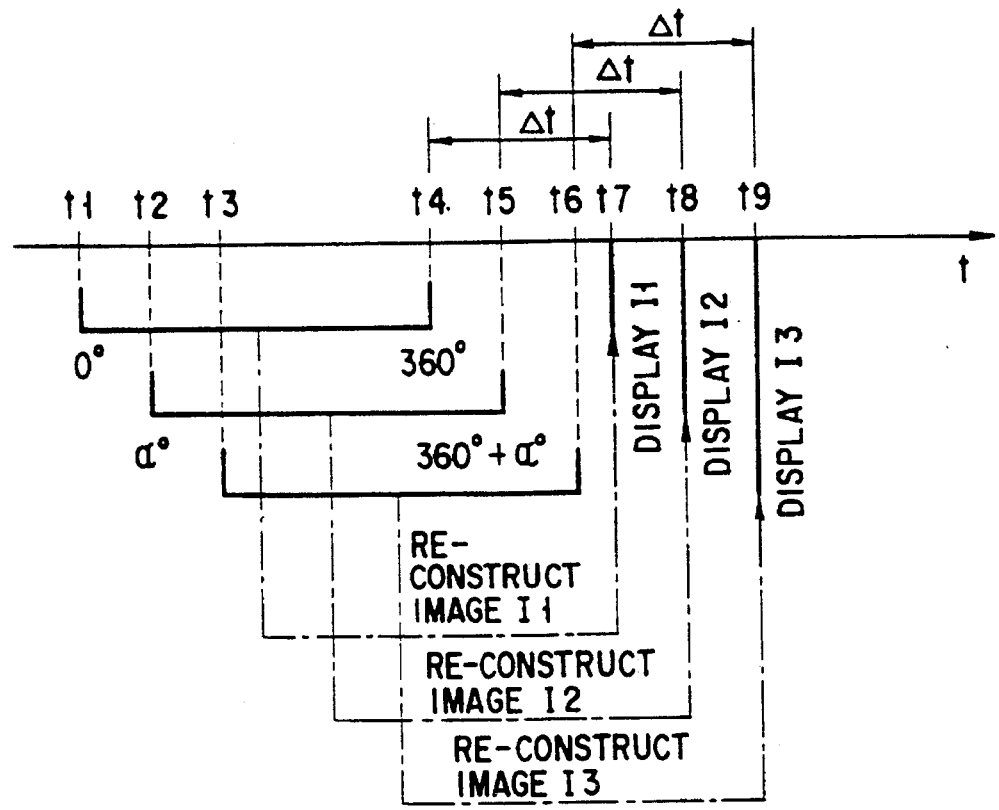
FIGS. 7A and 7B illustrate timing by which data acquisition and display are performed during a continuous scan
Figure 7B:
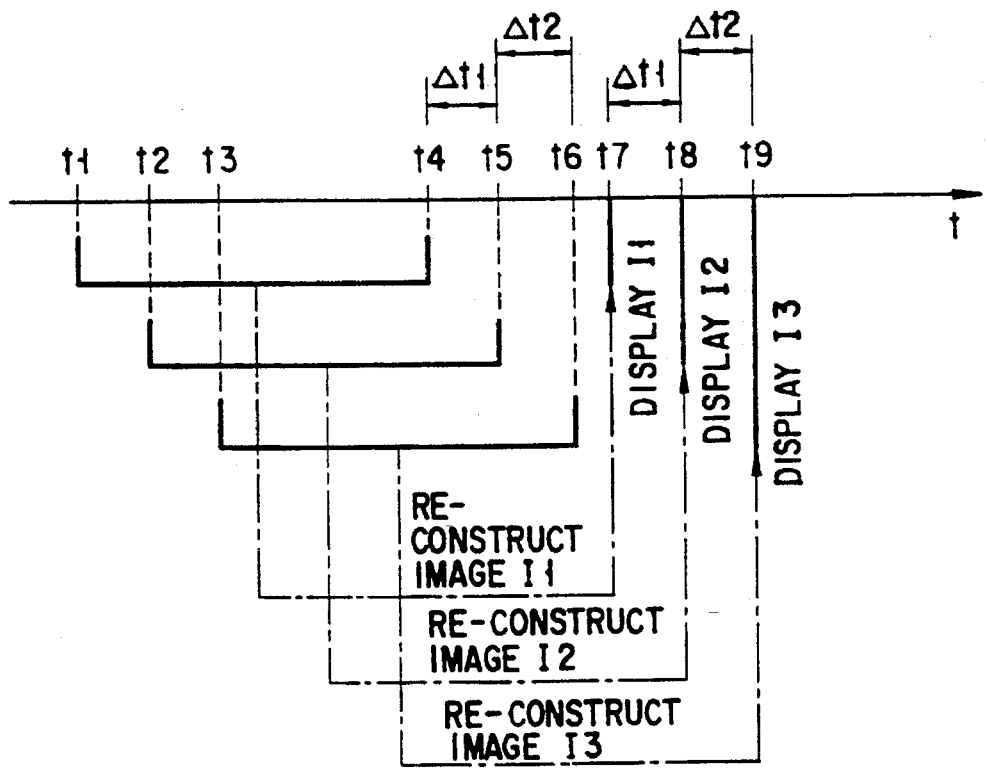
Figure 8:
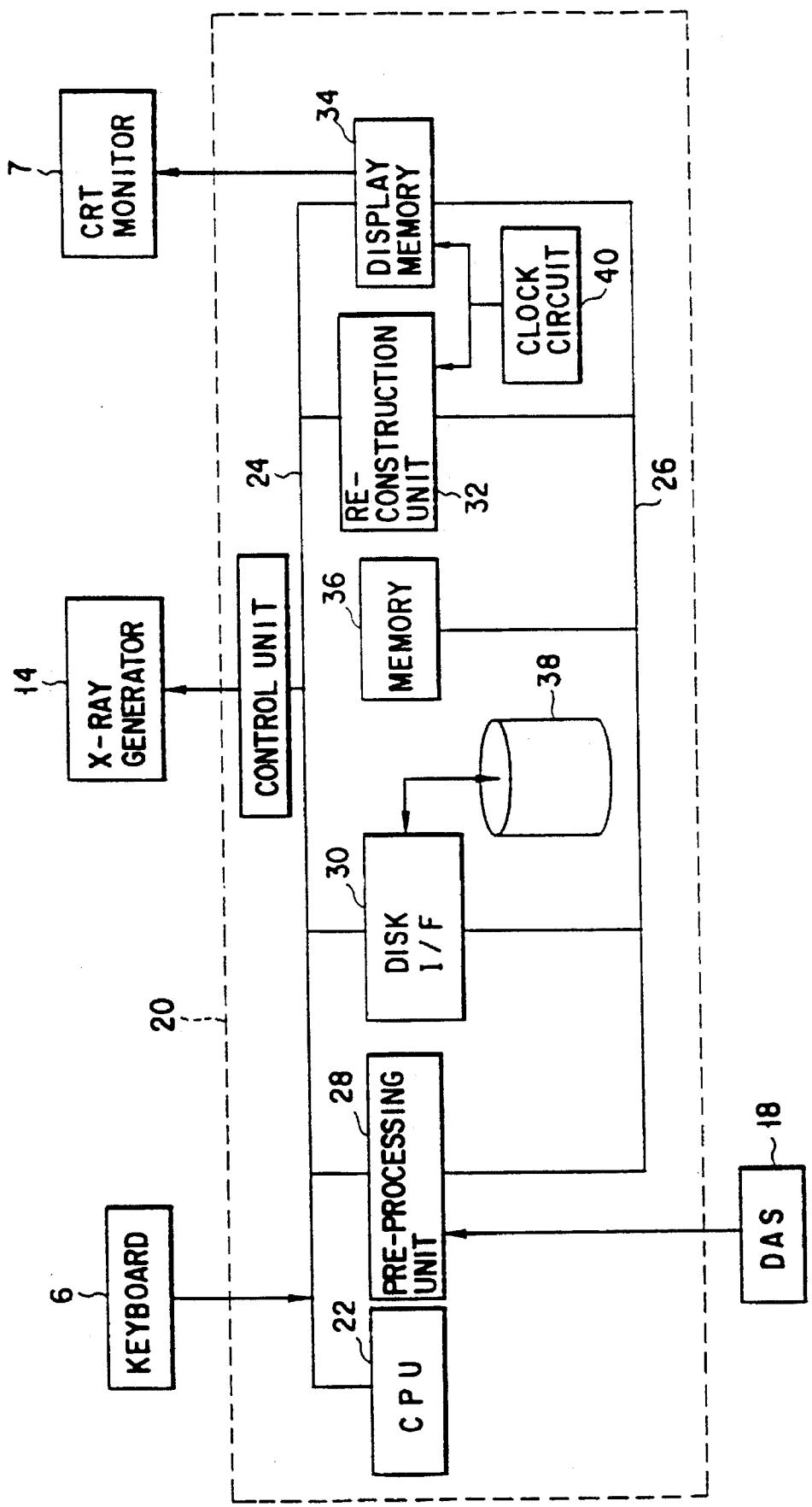
FIG. 8 illustrates a modification of the control unit of FIG. 4.

Important to the real-time cinetomography are faithful reproduction of the speed of internal movements of a human body as well as reduction of the time that elapses from scan to tomography image display. For example, if two tomography images the projection data of which were acquired at an interval of one second are displayed at an interval of 1.1 seconds it cannot be said that the internal movements of the human body are reproduced. In the present embodiment, as shown in FIG. 7A, the time differential $\Delta t$ between the moment that a scan operation for a single tomography image is completed (data acquisition is completed) and the moment that the display of that tomography image is started is made the same for all tomography images I1, I2, I3, etc. In other words, as shown in FIG. 7B, the tomography images I1 and I2 are displayed at a time interval equal to the time interval $\Delta t1$ between their scan operations and the tomography images I2 and I3 are displayed at a time interval equal to the time interval $\Delta t2$ between their scan operations. Other images are displayed in the same manner. This equalizes the scan and display time scales, permitting the internal movements of a human body to be reproduced faithfully. In general, the time $\Delta t'$ from a scan operation to the time when tomography image data has been written into the display memory 34 varies with load conditions on the CPU 22. For example, the time will become long when a scan is made or short when no scan is made. If, therefore, reading of tomography image data is started immediately after it has been written into the display memory 34, then the internal movements of a body will not be reproduced. In the present embodiment, the time difference between the termination of a scan operation and the start of tomography image data readout (the start of image display) is fixed at least to more than the time (maximum time) that the CPU 22 undergoes the maximum load so that the internal movements of a human body under examination will be reproduced. This time control can be implemented by the use of existing techniques. For example, as shown in FIG. 4, the CPU 22 may controls the timing of operations of the components 28, 32, 34, and 36. As shown in FIG. 8, the reconstruction unit 32 and the display memory 34 may share clocks. Though not shown, each of the preprocessing unit 28 and the display memory 34 may incorporate a timer circuit. In this case, the preprocessing unit informs the controller of the display memory of the time of arrival of projection data for a single image, thereby causing tomography image data to be read from the display memory 34 after a lapse of a given period of time from that time.

As described above, the present embodiment permits the movements of objects to be observed in real time like motion picture while making a continuous scan. This permits support for biopsy by observing the blood flow (the flow of a contrast medium), taking a tomography image at the optimum timing, watching the movement of a catheter, or watching variations in the blood flow.

Speeding up the data acquisition can be achieved by using a plurality of X-ray tubes in the case of the third-generation CT apparatus, increasing the rotational speed of the X-ray tube, or using the fifth-generation CT apparatus. The fifth-generation CT apparatus uses a number of X-ray tubes arranged around a human body or a hanging-bell-like X-ray tube having such an annular cathode as surrounds a human body within the aperture of the gantry.

Moreover, to speed up data acquisition and reconstruction, a half-scan reconstruction method can be used, which reconstructs an image from projection data for a scanning angle smaller than 360°, for example, 180°.

Furthermore, to check an increase in the amount of exposure of human bodies to X-rays caused by the continuous scan, use may be made of an X-ray generator which is capable of generating X-rays at a low tube current or an X-ray generator which is capable of generating pulsed X-rays. The dose of X-rays depends greatly on the product of the tube current mA and the X-ray emission time t (seconds), mA×s. For this reason, the tube current has only to be decreased in order to reduce the dose of X-rays. However, since the CT apparatus is generally designed such that X-rays are produced at a tube current in the range of some hundreds of milliamperes, the X-ray tube control method must be changed so that X-rays can be produced at a low tube current in the range of some tens of milliamperes.

To reduce the amount of exposure to X-rays, pulsed X-rays can be used in place of continuous X-rays which are used in most of the present CT apparatuses. For example, the use of pulsed X-rays of a duty cycle of 50% as shown in FIG. 9 can achieve a reduction of one half in the dose as compared with the use of continuous X-rays. Alternatively, the control circuit in the console 3 may be equipped with a circuit for on-off controlling the emission of X-rays at a high speed so as to allow an operator to turn x-rays on and off at his or her discretion with the X-ray tube and the detector array kept rotating and the X-ray tube pre-heated. This permits frequent on and off control of X-rays to be performed easily and at a high speed, thus reducing the amount of exposure of a human body to X-rays.

Furthermore, by providing a filter 40 at the X-ray outlet of the X-ray tube 12 or in the neighborhood of the upper slit 42 as shown in FIG. 10, the amount of exposure of a human body to X-rays can also be reduced. The filter 40 may be made of aluminum, copper, Teflon, or molybdenum. In addition, by designing the filter 40 and/or a wedge 43 such that their thickness can be varied, the amount of exposure can be reduced.

Although, in the above description, tomography image data is not stored on the magnetic disk 38, a tomography image being displayed on the CRT monitor 7 may be recorded on a video tape by the use of a video recorder. After the termination of scan, tomography images can be reproduced from the recorder in the mode of frame-by-frame forwarding or reverse forwarding, permitting easy diagnosis. Reconstructed image data and side information may be recorded in digital form. To display recorded data, reproduced data is fed into the CRT monitor 7 via the display memory 34. Recording image data in digital form permits postprocessing, such as deletion, to be performed easily.

Figure 11:
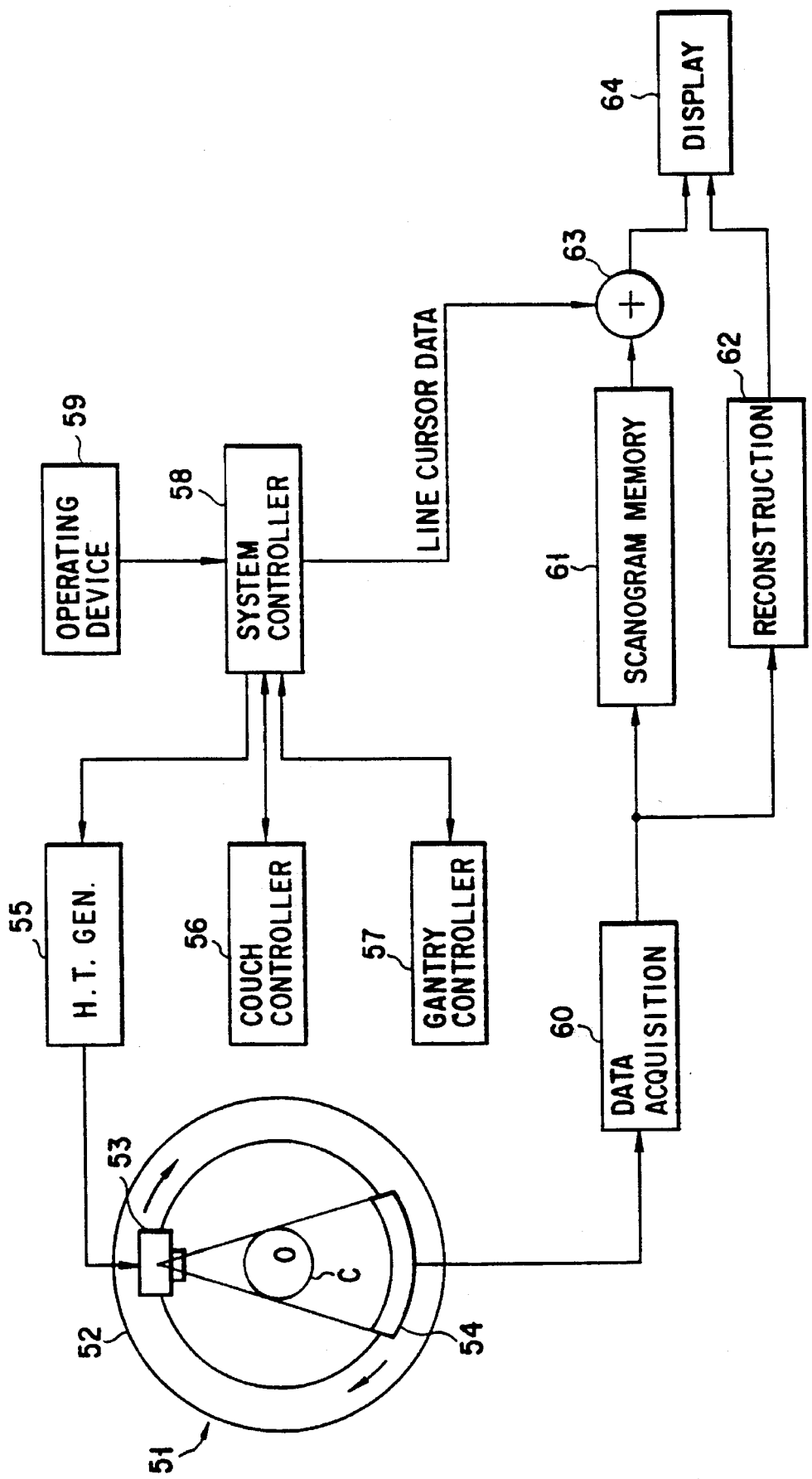
FIG. 11 is a block diagram of a computerized tomography apparatus according to a second embodiment of the present invention.

Referring now to FIG. 11, there is illustrated a computerized tomography apparatus according to a second embodiment of the present invention. The second embodiment will be described herein as comprising the third-generation (R/R) computerized tomography apparatus in which the x-ray tube and the detector array rotates around a subject under examination while facing each other. However, the second embodiment may be directed to the fourth-generation (R/S) computerized tomography apparatus in which the X-ray tube alone rotates and the detector array of a 360°-length is fixed.

In a gantry 51, an X-ray tube 53 and a multichannel X-ray detector array 54 are mounted on a rotation member 52 so that, in operation, they can rotate while facing each other with a human body under examination interposed therebetween. A gantry control unit 57 powers a driving unit such as a motor to drive the rotation member 52 into rotation. The X-ray tube and the detector array are electrically connected to a high-tension generator 55 and a data acquisition system 60, respectively, through slip rings not shown so that projection data can be acquired successively for angles from 0° to more than 360°. A fan beam of X-rays is emitted from the focus of the X-ray tube 53 powered from the high-tension generator 55. The X-ray detector array 54 comprises a number of detector elements arranged in the form of a circular arc with center at the focus of the X-ray tube. The gantry 51 is formed in its central portion with an aperture (not shown) to accommodate a portion of a human body under examination. The gantry is installed on the floor by a tilting base so that it can tilt with respect to the vertical axis. In front of the gantry 51 is placed a couch not shown. On the top of the couch is placed a top board on which a human body is to be laid down. The top board is movable on the couch not only in the direction of its long axis so that is can move toward or away from the gantry but also in the direction of its short axis perpendicular to the long axis. The top board is electrically driven by a driving unit to move independently in each direction. A couch control unit 56 supplies control signals to the top board driving unit to move the top board in the direction of its long axis and in the direction of its short axis. This permits a to-be-examined planar slice of a human body laid down on the top board to be placed in the proper position for examination.

A data acquisition system 60 acquires projection data representing X-ray transmission through the body section on the basis of outputs of the X-ray detector array 54. The projection data from the data acquisition system 60 is sent to a scanogram memory 61 at the time of capture of a scanogram. At the time of scan, on the other hand, the projection data is sent to a reconstruction unit 62. The scanogram is an X-ray projection image observed from one direction and obtained while the top board is moved with the rotation member 52 stopped. At the time of tomography, scanogram data is read from the scanogram memory 61 repeatedly at a given period, combined in an adder 63 with line cursor data from a system controller 58, and sent, together with tomography image data reconstructed in the reconstruction unit 62, to an image display unit 64. At the time of tomography, a scanogram is displayed simultaneously with tomography images on the screen of the display unit 64. To the system controller 8 is coupled an operating device 59 such as a trackball or joystick. When an operator moves the operating device, the line cursor moves on the scanogram accordingly. The position of the line cursor on the scanogram corresponds to the position of a slice of interest of a human body for which data acquisition is actually carried out. When the line cursor is moved on the scanogram, the system controller 8 instructs the couch control unit 56 to move the top board so that the slice corresponds in position to the line cursor.

Next, the operation of the present embodiment will be described. FIG. 12 illustrates an example of a display screen at the time of tomography. The tomography has been described in connection with the first embodiment and its description is omitted here. Before tomography is started, a scanogram is captured. With the rotation member 2 fixed at an angle of, say, 0°, the emission of X-rays and data acquisition are repeated, during which time the top board is moved continuously or intermittently. Note that the emission of X-rays and data acquisition may be repeated only at an angle of rotation of, say, 0° while the rotation unit 2 continues to rotate. On the basis of outputs of the X-ray detector array 54 the data acquisition system 60 repeats the acquisition of projection data synchronously with X-ray emission. The projection data is sent to the scanogram memory 11 and stored therein. As described above, the scanogram is an X-ray projection image and projection data acquired by the data acquisition system 60 is used as scanogram data as it is.

Next, the computerized tomography is started, which is described herein as single-slice tomography. In the computerized tomography, X-ray emission and data acquisition are repeated while the rotating member 52 continues to rotate, so that projection data is acquired successively from angles from 0° to more than 360°. Each time projection data required to reconstruct a tomography image is acquired, that a tomography image is reconstructed in the reconstruction unit 62, then sent to the display unit 64. After being read from the scanogram memory 61, scanogram data is added with line cursor data in the adder 63, then sent to the display unit 64. In the display unit 64, as shown in FIG. 12, the tomography image and the scanogram are combined, then displayed simultaneously on the same screen. The line cursor on the scanogram indicates the position of the current slice of a human body being examined.

When a change from one slice (a body section for diagnosis) to another is desired, the operator moves the operating device 59 to move the line cursor on the scanogram along the body axis. In response to the movement of the line cursor on the scanogram, the system controller 56 instructs the couch control unit 56 to move the top board in the direction of its length. Thus, the top board is moved to follow the line cursor, whereby a slice corresponding in position to the line cursor is selected for subsequent scanning. In practice, it is convenient to move roughly the line cursor to a desired position on the scanogram and then to make fine adjustments in the position of the cursor while watching a tomography image displayed in real time.

By moving the operating device 59, the line cursor can also be moved on the scanogram in the direction of the width perpendicular to the body axis. In response to this movement of the line cursor on the scanogram, the system controller 8 instructs the couch control unit 56 to move the top board in the direction of the width. Thereby, the human body to be examined can be placed in position for reconstruction so that a desired body region is included in tomography images.

Thus, by moving the line cursor on a scanogram, a change from one slice to another can be made easily in a short time.

while the top board is moving, or while the gantry 51 is tilted as shown in FIG. 14, the gantry control unit 57 permits the rotation unit 52 to continue to rotate, and the high-tension generator 55 temporarily interrupts power supply to the X-ray tube 53 to stop the emission of X-rays under the control of the system controller 58 as shown in FIG. 13. With the rotation member 52 continuing rotation, after a desired slice of a human body is placed in position as a result of movement of the top board, power supply from the high-tension generator 55 to the X-ray tube 53 can be restarted to resume the acquisition of tomography image data immediately. If the rotation member 52 is stopped while the top board 65 is moving on the couch, it would be required to wait until the rotation member has reached a given speed of rotation after the termination of the movement of the top board. The stoppage of the emission of the X-rays during the movement of the top board can prevent unwanted exposure of a human body under examination to X-rays.

Figure 15:
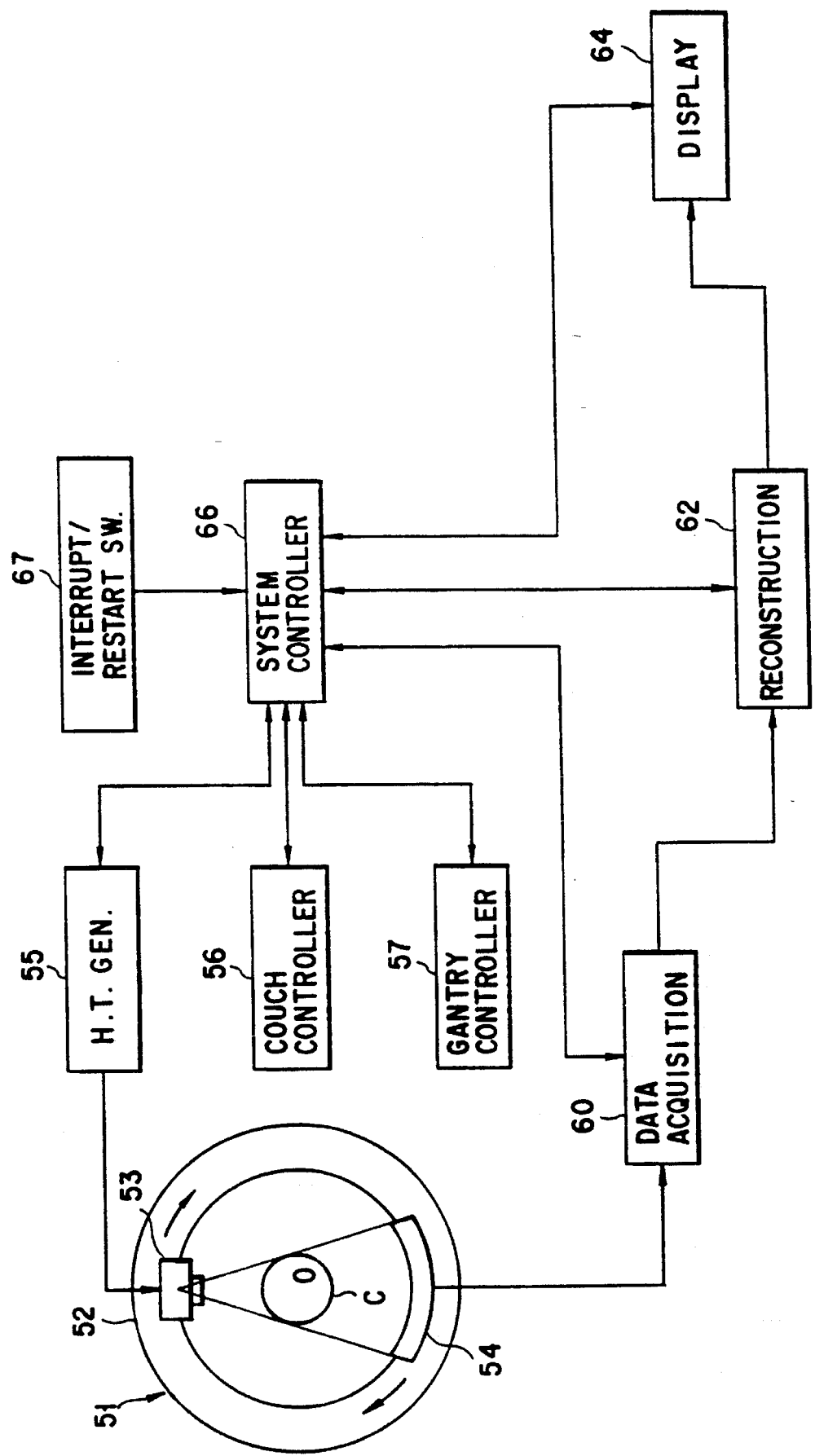

Next, a third embodiment of the present invention will be described. FIG. 15 illustrates the entire structure of a computerized tomography apparatus according the third embodiment of the present invention. In this figure, like reference numerals are used to denote corresponding components to those in, FIG. 11 and their description will be omitted here. In the third embodiment, use may be made of a helical scan system in which data acquisition is performed while the X-ray tube 53 moves along a herical orbit around a human body under examination as shown in FIG. 16A or a multi-slice scan system in which a single scan is made successively for each of discrete slices. The present embodiment is described as using the herical scan system. In the herical scan, data acquisition is repeated while the rotation member 52 makes continuous rotation and the top board moves at a constant speed in one direction. Projection data is represented by D(CH, $\phi$, Z) where CH stands for a channel, $\phi$ stands for an angle of rotation of the rotation member 52, and Z stands for the position of the top board in the direction of its length (in the direction of the body axis). During the herical scan, Z varies with $\phi$ because the top board moves continuously,. In order to reconstruct a single tomography image, it is required to acquire projection data for angles 0° to 360° for the same position (Z) of the top board. Since Z varies with $\phi$ in projection data obtained by the herical scan, projection data actually obtained for angles 0° to 720° is converted to projection data for 0° to 360° in which the top board position Z is standardized to the center position Zc (Zc=(Z1–Zn)/2) in the z range (Z1 to Zn) of the 0° -to-720° projection data by means of distance interpolation as shown in FIG. 16B. The position of a slice for a herical-scan tomography image is defined by Zc.

If, when a herical scan is being made, an operator enters an Interrupt instruction via an operating device 67, a system controller 66 stops the movement of the top board, the emission of X-rays, and the data acquisition. However, as in the second embodiment, it is desirable to keep the rotation member 52 rotating from the standpoint of quick restart of tomography. There is Some time lag between data acquisition and tomography image display because some time is needed for distance interpolation and reconstruction. Because of the existence of this time lag and the principle of the distance interpolation the position of a slice for a tomography image being displayed and the current position of the top board will not inevitably coincide when an interruption is instructed by the operator.

When the tomography is interrupted, the system controller 66 moves the top board backward to the position at the time the tomography image, i.e., the latest tomography image, was displayed when the interruption was instructed before tomography is restarted. When a Restart instruction is entered via the operating device 67, the system controller 66 instructs the couch control unit 56 to restart the movement of the top board, whereby tomography is restarted. In this case, since the rotation unit 52 is kept rotating and the top board has been returned to the slice position for the latest tomography image displayed when the interruption was instructed, the emission of X-rays has only to be restarted.

By specifying any one of a plurality of tomography images already reconstructed, it is also possible to return the top board automatically to the slice position for that tomography image specified. Moreover, by specifying any two of a plurality of tomography images already reconstructed, it is also possible to carry out tomography while causing the top board to move from one of the slice positions for the two tomography images to the other and back. Furthermore, if, when a herical scan is made while the tilt angle of the gantry 51 is changed, its tilt angles are stored in a one-to-one correspondence with top board positions, then it will be possible to return the gantry to a tilt angle at the time of acquisition of tomography image data displayed when an interruption was instructed.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A computerized tomography apparatus comprising:

acquiring means for acquiring a projection data set;

reconstructing means for reconstructing tomography data of one frame based on the projection data set;

displaying means for visually displaying the tomography data; and means for selecting one of a real-time mode and a time-sharing mode, wherein, in the real-time mode, said acquiring means repeatedly acquires projection data sets, said reconstructing means repeatedly reconstructs the tomography data in synchronism with acquiring the projection data sets, and said displaying means displaying the tomography data as a moving image in synchronization with acquiring the projection data sets, and wherein, in the time-sharing mode, said acquiring means acquires the projection data set, said reconstructing means reconstructs the tomography data asynchronously with acquiring the projection data set, and said displaying means displays the tomography data asynchronously with acquiring the projection data set.

2. The apparatus according to claim 1, wherein said reconstructing means reconstructs the tomography data of one frame in a shorter time than a time required to acquire one projection data set in the real-time mode.

3. The apparatus according to claim 1, wherein said displaying means displays the tomography data after a predetermined interval from an acquisition of the projection data set.

4. The computerized tomography apparatus according to claim 1, wherein said acquiring means comprises:

means for generating x-rays at a first intensity in the real-time mode; and means for generating x-rays at a second intensity in the time-sharing mode, wherein the first intensity is lower than the second intensity.

5. The computerized tomography apparatus according to claim 1, wherein said acquiring means comprises means for generating x-rays, wherein an intensity of the x-rays in the real-time mode is lower than in the time-sharing mode.

* * * * *